United States Patent [19]

Lee

[11] Patent Number: 5,565,410
[45] Date of Patent: *Oct. 15, 1996

[54] HETEROCYCLIC DIONES AS PESTICIDES AND PLANT GROWTH REGULATORS

[75] Inventor: Shy-Fuy Lee, Sunnyvale, Calif.

[73] Assignee: Sandoz Ltd., Basel, Switzerland

[*] Notice: The term of this patent shall not extend beyond the expiration Date of Pat. No. 5,336,662.

[21] Appl. No.: 232,919

[22] Filed: Apr. 25, 1994

Related U.S. Application Data

[62] Division of Ser. No. 994,048, Dec. 14, 1992, Pat. No. 5,336,662, which is a continuation of Ser. No. 902,609, Jun. 23, 1992, abandoned, which is a continuation of Ser. No. 604,708, Oct. 25, 1990, abandoned, which is a continuation-in-part of Ser. No. 497,154, Mar. 20, 1990, abandoned, which is a continuation-in-part of Ser. No. 343,093, Apr. 25, 1989, abandoned.

[51] Int. Cl.$^6$ ........................ A01N 43/72; A61K 31/535; C07D 265/02
[52] U.S. Cl. ........................ 504/223; 514/228.8; 544/63; 544/71
[58] Field of Search ............................... 504/223; 544/63, 544/71; 514/228.8

[56] References Cited

U.S. PATENT DOCUMENTS

| | | | |
|---|---|---|---|
| 4,552,585 | 11/1985 | Chang | 71/88 |
| 4,695,673 | 9/1987 | Heather et al. | 568/310 |
| 4,921,526 | 5/1990 | Lee et al. | 71/86 |
| 5,006,150 | 4/1991 | Lee et al. | 71/88 |
| 5,061,310 | 10/1991 | Ooms et al. | 504/223 |
| 5,089,046 | 2/1992 | Lee et al. | 71/103 |
| 5,336,662 | 8/1994 | Lee | 504/223 |

FOREIGN PATENT DOCUMENTS

| | | | |
|---|---|---|---|
| 2098589 | 2/1972 | France. | |
| 2207425 | 2/1989 | United Kingdom | C07D 311/76 |

Primary Examiner—Mukund J. Shah
Assistant Examiner—Pavanaram K. Sripada
Attorney, Agent, or Firm—Lynn Marcus-Wyner, Ph.D.

[57] ABSTRACT

Substituted 3,5-dioxo-3,4,5,6-tetrahydrooxazines as herbicides.

15 Claims, No Drawings

HETEROCYCLIC DIONES AS PESTICIDES AND PLANT GROWTH REGULATORS

This application is a divisional of Ser. No. 07/994,048 filed Dec. 14, 1992 now issued as U.S. Pat. No. 5,336,662 which is a continuation of Ser. No. 07/902,609 filed Jun. 23, 1992, now abandoned, which is a continuation of Ser. No. 07/604,708 filed Oct. 25, 1990, now abandoned, which is a continuation-in-part of Ser. No. 07/497,154 filed Mar. 20, 1990, now abandoned, which is a continuation-in-part of Ser. No. 07/343,093 filed Apr. 25, 1989, now abandoned.

The present invention concerns substituted 3,5-dioxo-3, 4,5,6-tetrahydrooxazines as herbicides, processes and intermediates for their preparation, compositions containing them and their use as herbicides and acaricides.

More particularly, the invention concerns compounds of formula I

wherein

A represents the group (i)

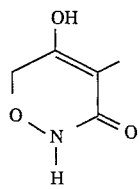

in which any free hydrogen may be replaced by a substituent; and

B represents an optionally substituted aryl or heteroaryl group.

Examples of substituents which may be present on ring (i) include alkyl, carboxy, alkoxycarbonyl and phenyl, itself optionally substituted, or a spiro-ring. The hydroxy group may be substituted eg. by alkyl, alkylcarbonyl, arylcarbonyl, alkoxycarbonyl, aminocarbonyl (optionally substituted), alkylsulphonyl, phosphonyl (optionally substituted) phosphinyl (optionally substituted) or may form salts.

Examples of substituents which may be present on B include one or more alkyl, haloalkyl, alkoxy, haloalkoxy, halogen, nitro, cyano, alkyl $S(O)_{n'}$, haloalkyl $S(O)_{n'}$, cyanoalkyl $S(O)_{n'}$, alkylsulphonyloxy, haloalkyl-sulphonylamino (including mono and dialkylamino), phenyl $S(O)_{n'}$, benzyl $S(O)_{n'}$, amino, alkylamino, dialkylamino, alkylcarbonyl, alkoxycarbonyl, aminosulphonyl, alkylaminosulphonyl, dialkylaminosulphonyl, alkylcarbonylamino, alkylcarbonylalkylamino, formylamino, formylalkylamino groups. n' is 0, 1 or 2.

B is preferably phenyl, unsubstituted or substituted, as mentioned above.

U.S. Pat. No. 4,695,673 describes a wide range of acylated 1,3-dicarbonyl compounds and their use as herbicides but makes no reference to or suggestion of the 3,5-dioxotetrahydrooxazine ring characterizing the compounds of the present invention.

A particular group of compounds of formula I is comprised of those of formula Ia

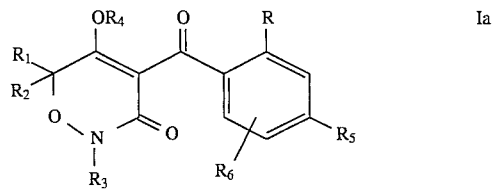

wherein, each of $R_1$, $R_2$ and $R_3$ is independently hydrogen, $C_{1-8}$alkyl, carboxyl, $C_{1-8}$alkoxycarbonyl, phenyl or phenyl substituted by one to three groups as $R_5$, or $R_1$ and $R_2$ together form a $C_{3-6}$alkylene bridge $R_4$ is hydrogen, $C_{1-8}$alkyl, $C_{1-8}$alkylcarbonyl, $C_{1-8}$alkoxycarbonyl, —C(O)NR$_7$R$_8$, $C_{1-8}$alkylsulphonyl, P(O)—(OR$_9$)$_2$, R$_7$P(O)—OR$_9$, benzoyl or a cation.

R is $C_{1-8}$alkyl optionally substituted by 1 to 6 halogen atoms, $C_{1-8}$-alkoxy optionally substituted by 1 to 6 halogen atoms, $C_{1-8}$alkyl-carbonyl, $C_{1-8}$alkoxycarbonyl, NR$_7$R$_8$, $O_n$S(O)$_n$R$_{10}$, NR$_7$SO$_2$R$_8$, halogen cyano or nitro.

each of $R_5$ and $R_6$ is independently hydrogen or selected from the meanings given for R; or $R_5$ and $R_6$ together form the group —Y—W—Z—;

each $R_7$ and $R_8$ is independently hydrogen or $C_{1-8}$alkyl;

$R_9$ is $C_{1-8}$alkyl;

$R_{10}$ is $C_{1-8}$alkyl optionally substituted by 1 to 6 halogen atoms;

W is —(CR$_{11}$R$_{12}$)$_t$—(CR$_{13}$R$_{14}$)$_{t'}$- or sulphonyl;

each of Y and Z is independently oxygen, sulphur, sulphonyl, carbonyl or CR$_7$R$_8$ with the proviso that Y and Z are attached to adjacent carbon atoms;

each of $R_{11}$ and $R_{12}$ is independently hydrogen, halogen or $C_{1-8}$alkyl optionally substituted by 1 to 6 halogen atoms or together form an oxo group;

each of $R_{13}$ and $R_{14}$ is independently hydrogen; halogen or $C_{1-8}$alkyl optionally substituted by 1 to 6 halogen atoms;

n is 0 or 1;

n' is 0, 1 or 2;

t is 1 or 2;

t' is 0 or 1.

In the above definitions, halogen is conveniently selected from chloro, bromo and fluoro, $C_{1-8}$alkyl moieties, preferably have 1 to 4 carbon atoms.

Each of $R_1$, $R_2$ and $R_3$ is preferably hydrogen, $C_{1-4}$alkyl especially hydrogen or $C_{1-3}$alkyl.

R conveniently signifies $C_{1-4}$alkyl optionally substituted with halogen, —(O)$_n$-S(O)$_{n'}$-C$_{1-4}$alkyl, halogen or nitro. It is preferably methyl, CF$_3$, $C_{1-3}$alkylsulfonyl, $C_{1-3}$alkylsulfonyloxy, chloro, bromo or nitro.

$R_5$ is preferably bromo, chloro, fluoro, haloalkyl, haloalkoxy, SC$_{1-4}$alkyl, OSO$_2$C$_{1-4}$alkyl, SO$_2$C$_{1-4}$alkyl, OSO$_2$C$_{1-4}$haloalkyl, NR$_7$SO$_2$ C$_{1-4}$alkyl, or, together with $R_6$, the group —Y—W—Z—. It is more preferably chloro, fluoroalkyl, fluoroalkoxy, $C_{1-3}$alkylsulfonyl or $C_{1-3}$alkylsulfonyloxy, or, together with $R_6$, methylenedioxy.

$R_6$ is preferably hydrogen, $C_{1-4}$alkyl, $C_{1-4}$alkoxy, bromo, chloro or, together with $R_5$, the group —Y—W—Z—; it is more preferably hydrogen, methoxy or chloro, or, together with $R_5$, methylenedioxy.

$R_4$ is conveniently hydrogen, $C_{1-4}$alkyl, $C_{4-8}$alkylcarbonyl, benzoyl, $C_{1-4}$alkylsulfonyl or a cation. It is preferably hydrogen, methyl, ethyl, t-butylcarbonyl, isobutylcarbonyl, benzoyl or methylsulfonyl. As a cation $R_4$ is preferably an alkali metal such as $Na^+$, $K^+$, $Li^+$ or an ammonium cation.

Examples of particularly preferred substituents are for $R_1$ and $R_2$ each = a) H, $C_{1-4}$alkyl, phenyl or phenyl substituted by one to three groups as $R_5$
b) H, $C_{1-4}$alkyl phenyl or phenyl substituted by one to three groups as R
c) H, $C_{1-3}$alkyl
d) H, $CH_3$
e) $C_{1-3}$alkyl $R_3$ = a) $C_{1-8}$alkyl
b) $C_{1-4}$alkyl
c) $CH_3$, $C_2H_5$ $R_4$ = H
R = a) $NO_2$, Cl, $CF_3$
b) $NO_2$, Cl
c) $NO_2$ $R_5$ = a) Cl, Br, F, $SO_2-R_{10}$, $SR_{10}$, $OSO_2R_{10}$, $CF_3$, $OCF_3$, $OCF_2H$
b) Cl, $OSO_2R_{10}$, $SR_{10}$, $CF_3$, $OCF_3$, $OCF_2H$ $R_6$ = H
$R_{10}$ = a) $C_{1-8}$alkyl optionally halogen substituted
b) $C_{1-3}$alkyl optionally halogen substituted
c) $C_{1-3}$alkyl Combinations of these substituent meanings are especially preferred.

Three particularly preferred single compounds are 2,6,6-trimethyl-4-(4-chloro-2-nitrobenzoyl)-2H-1,2-oxazine-3,5-(4H,6H)-dione; 2,6,6-trimethyl- 4-(4-methylthio-2-nitrobenzyl)-2H-1,2-oxazine-3,5-(4H,6H)-dione; and 2,6,6-trimethyl-4-(4-difluoromethoxy-2-nitrobenzyl)-2H-1,2-oxazine-3,5-(4H,6H)-dione.

The compounds of the present invention of formula I are new substances which can be prepared by methods analogous to methods known in the art, such as those described in European Patent Application EP 186,117 and references cited therein. More particularly, they can be obtained by, for example: rearranging an enol ester of formula (II)

wherein A' represents the group (ii)

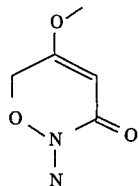

in which any free hydrogen may be replaced by a substituent and B is as defined above to give a compound wherein the OH group in group (i) is unsubstituted (e.g. $R_4$=H in compounds Ia).

This rearrangement is conveniently effected by reacting the compound of formula II with a cyanide source and a moderate base.

For example, the reaction may be carried out in the presence of a catalytic amount of a source of cyanide anion and/or hydrogen cyanide, together with a molar excess, with respect to the enol ester, of a moderate base. The reaction is conveniently carried out in a solvent which is inert under the reaction conditions, e.g. 1,2-dichloroethane, toluene, acetonitrile, methylene chloride, ethyl acetate, dimethylformamide (DMF) and methyl isobutyl ketone (MIBK). In general, depending on the nature of the reactants and the cyanide source, the rearrangement may be conducted at temperatures up to about 80° C. In some cases, for instance when there is a possible problem of excessive by-product formation, the temperatures should be kept at about 40° C. maximum.

Preferred cyanide sources are alkali metal cyanides such as sodium and potassium cyanide; cyanohydrins of methyl alkyl ketones having from 1–4 carbon atoms in the alkyl groups, such as acetone or methyl isobutyl ketone cyanohydrins; cyanohydrins of benzaldehyde or of $C_2$–$C_5$ aliphatic aldehydes such as acetaldehyde, propionaldehyde, etc., cyanohydrins; zinc cyanide; tri(lower alkyl) silyl cyanides, notably trimethyl silyl cyanide; and hydrogen cyanide itself. Among cyanohydrins the preferred cyanide source is acetone cyanohydrin. The cyanide source is used in an amount up to about 50 mole percent based on the enol ester. Generally about 1–10 mole % of the cyanide source is preferred.

By the term "moderate base" is meant a substance which acts as a base yet whose strength or activity as a base lies between that of strong bases such as hydroxides (which could cause hyrolysis of the enol ester) and that of weak bases such as bicarbonates (which would not function effectively). Moderate bases suitable for use in this reaction include both organic bases such as tertiary amines and inorganic bases such as alkali metal carbonates and phosphates. Suitable tertiary amines include trialkylamines such as triethylamine, trialkanolamines such as tri-ethanolamine, and pyridine. Suitable inorganic bases include potassium carbonate and trisodium phosphate. The base is used in an amount of from about 1 to about 4 moles per mole of enol ester, preferably about 1.3–2 moles per mole.

When the cyanide source is an alkali metal cyanide, particularly potassium cyanide, a phase transfer catalyst may be included in the reaction. Particularly suitable phase transfer catalysts are the Crown ethers.

Compounds of formula I where the OH group in the group (i) is substituted can be prepared by reacting a compound of formula I wherein the OH group in the group (i) is unsubstituted with either a) the group $R_{40}$-OH and a catalyst, or
b) the group $R_{40}$-Q and a moderate base, wherein Q is a halogen atom, to give a compound of formula I where $R_{40}$ is the desired substituent.

The above reaction a) is carried out in the presence of a catalyst such as concentrated sulfuric acid. The reaction is conveniently carried out in a solvent which is also the reactant such as methanol, and at an elevated temperature.

The above reaction b) is carried out in the presence of a moderate base such as triethylamine or pyridine and conveniently at RT or below.

The compounds of formula I may be recovered from the reaction mixture in which they are formed by working up by established procedures.

Compounds of the formula II corresponding to end products of formula Ia may be represented by the formula IIa

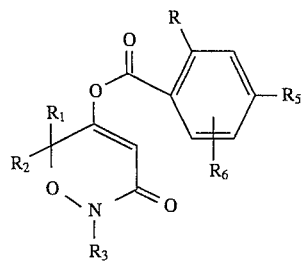

The compounds of formula IIa may be prepared by reacting a compound of formula III

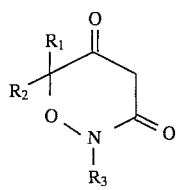

with a compound of formula IV

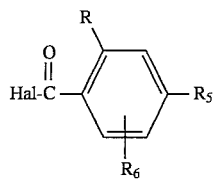

This reaction is carried out in the presence of a base such as triethylamine, potassium carbonate, pyridine, preferably triethylamine and in an inert solvent such as dichloromethane, acetonitrile, toluene, tetrahydrofuran, dimethylformamide. The reaction is conveniently carried out at RT or below.

The remaining compounds of formula II may be prepared analogously.

The compounds of formula III are new and also form part of the invention.

They may be prepared by decarboxylating a compound of formula V

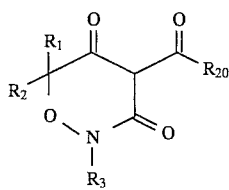

wherein $R_{20}$ is alkoxy, especially ethoxy or methoxy and $R_1$, $R_2$ and $R_3$ are as defined above. The reaction may be carried out at elevated temperatures e.g. 80°–90° and in an inert solvent such as e.g. wet dimethylsulfoxide.

The compounds of formula V may be prepared analogously to known methods e.g. according to the following reaction scheme.

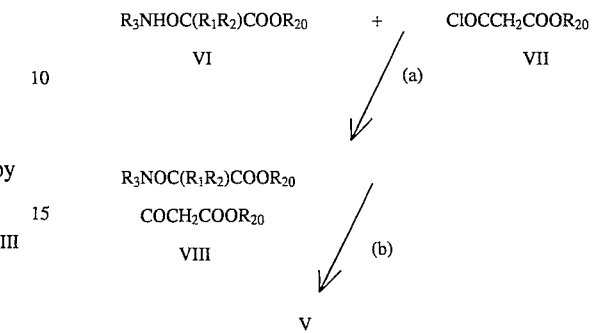

Reaction (a) may be carried out in an inert solvent such as dichloromethane and aqueous ether and in the presence of a base such as triethylamine or sodium carbonate at RT.

Reaction (b) may be carried out in an inert solvent such as toluene benzene or tetrahydrofuran in the presence of a base such as sodium methoxide or sodium hydride.

The remaining starting materials and reagents employed in the process described herein are either known or, insofar as they are not known, may be produced in a manner analogous to the processes described herein or to known processes [cf for compounds VI Kornowski et.al. Bull. Soc. Chim France 1966(2)683].

The compounds of this invention wherein the OH group in group (i) is unsubstituted can have four structural formulae because of tautomerism as illustrated as follows for formula Ia where $R_4$=H;

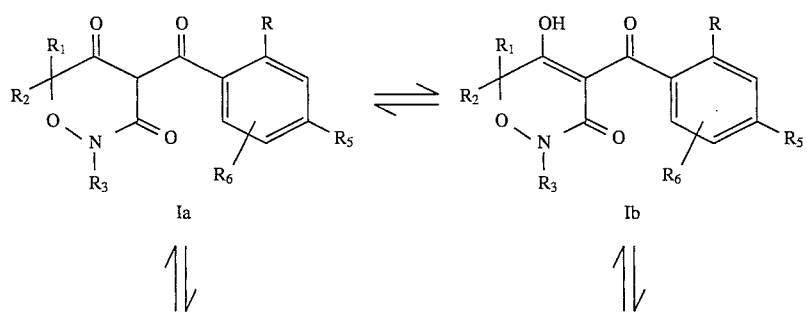

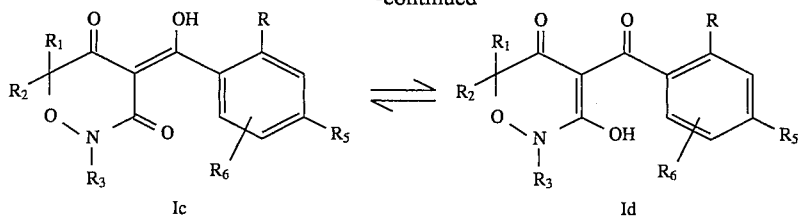

It will of course be readily appreciated that where $R_4$ is other than hydrogen such compounds may exist in forms Ib, Ic and Id or as mixtures of these forms.

The novel compounds of formula I are useful for the control of weeds, using pre- and/or post-emergent treatments. Compounds of formula I are also useful as plant growth regulators (PGRs) and acaricides. The compounds can be applied in the form of dusts, granules, solutions, emulsions, wettable powders, flowables and suspensions. Application of a compound of the present invention as herbicides is made according to conventional procedure to the weeds or their locus using an herbicidally effective amount of the compounds, usually from about one-tenth or less to ten pounds per acre. The application of a compound of the present invention to the "locus" of the weed includes application to the seeds, the plant (weed) or parts of the plant, or the soil.

Application of a compound of the present invention as an acaricide is made according to conventional procedure to the site of infestation using an acaricidally effective amount of the compound, usually 100 g/ha to 1 kg/ha.

The term "herbicide," as used herein, refers to an active ingredient which modifies the growth of plants because of phytotoxic or plant growth regulating properties so as to retard the growth of the plant or damage the plant sufficiently to kill it.

Compounds of the present invention, when applied as either post or pre-emergents, demonstrate high levels of herbicidal activity on broadleaf, grass and sedge weeds. They also exhibit selectivity in wheat (e.g. compound 6 in Table A); corn and cotton (e.g. compound 2 in Table A); and rice.

In the use of the compounds of formula I for combatting weeds and acari, a compound of formula I, or mixtures thereof, can conveniently be employed as pesticide compositions in association with acceptable diluent(s) for application to the weed, acari or their loci. Such compositions also form part of the present invention.

Methods of preparing suitable formulations which can be used with a compound of the present invention are described in the literature along with suitable liquid and solid carriers, such as in U.S. Pat. Nos. 4,192,669 and 4,163,661, which are incorporated herein by reference. The optimum usage of a compound of the present invention is readily determinable by one of ordinary skill in the art using routine testing such as greenhouse testing and small plot testing.

Suitable formulations contain from 0.01 to 99% by weight of active ingredient, from 0 to 20% of surfactant and from 1 to 99.99% of solid or liquid diluent(s). Higher ratios of surfactant to active ingredient are sometimes desirable and are achieved by incorporation into the formulation or by tank mixing. Application forms of a composition generally contain between 0.01 and 25% by weight of active ingredient. Lower or higher levels of active ingredient can, of course, be present depending on the intended use, the physical properties of the compound and the mode of application. Concentrate forms of a composition intended to be diluted before use generally contain between 2 and 90%, preferably between 5 and 81% by weight of active ingredient.

Useful formulations of the compounds of formula I include dusts, granules, suspension concentrates, wettable powders, flowable and the like. They are obtained by conventional manner, e.g. by mixing a compound of formula I with the diluent(s) and optionally with other ingredients.

Alternatively, the compounds of formula I may be used in micro-encapsulated form.

The compounds of formula I can be combined with a cyclodextrin to make a cyclodextrin inclusion complex for application to the weed, acari or their loci.

Agriculturally acceptable additives may be employed in the herbicidal compositions to improve the performance of the active ingredient and to reduce foaming, caking and corrosion, for example.

"Surfactant" as used herein means an agriculturally acceptable material which imparts emulsifiability, spreading, wetting, dispersibility or other surface-modifying properties. Examples of surfactants are sodium lignin sulfonate and lauryl sulfate.

"Diluent" as used herein means a liquid or solid agriculturally acceptable material used to dilute a concentrated material to a usable or desirable strength. For dusts or granules it can be e.g. talc, kaolin or diatomaceous earth, for liquid concentrate forms for example a hydrocarbon such as xylene or an alcohol such as isopropanol, and for liquid application forms e.g. water or diesel oil.

The compositions of this invention can also comprise other compounds having biological activity, e.g. compounds having similar or complementary acaricidal or herbicidal activity for broadspectrum weed control or compounds having antidotal, fungicidal, insecticidal or insect attractant activity.

The following examples are provided to illustrate the practice of the present invention. Temperature is given in degree Centigrade. RT means room temperature. Parts and percentages are by weight.

EXAMPLE I

Preparation of 2,6-dimethyl-4-(4-chloro-2-nitrobenzoyl)-2H-1,2-oxazine- 3,5-(4H,6H)-dione (Formula Ia $R_1=R_3=CH_3$; $R_2=R_4=R_6=H$; $R=NO_2$; $R_5=Cl$: Compound No. 1)

3.65 g of 2,6-dimethyl-5-(4-chloro-2-nitrobenzoyloxy)-6H-1,2-oxazine- 3-one is treated at r.t. with 3.06 ml of triethylamine and 0.3 ml of acetone cyanohydrin in 20 ml of acetonitrile (20 ml). After stirring overnight, the solution is concentrated to a small volume and then taken up in dichloromethane and water. The combined extracts are washed with dilute HCl, brine, dried and evaporated to yield an oil residue. The crude product is recrystallized from ether to give crystalline 2,6-dimethyl- 4-(4-chloro-2-nitrobenzoyl)-2H-1,2-oxazine-3,5-(4H,6H)-dione, M.P. 127.5° C.

Proceeding analogously to Example I the following compounds of formula I are obtained.

TABLE A

| Cpd | $R_1$ | $R_2$ | $R_3$ | $R_4$ | R | $R_5$ | $R_6$ | m.p. |
|---|---|---|---|---|---|---|---|---|
| 1 | $CH_3$ | H | $CH_3$ | H | $NO_2$ | 4-Cl | H | 127.5° |
| 2 | $CH_3$ | $CH_3$ | $CH_3$ | H | $NO_2$ | 4-Cl | H | 105° |
| 3 | $CH_3$ | $CH_3$ | $CH_3$ | H | Cl | 4-$SO_2CH_3$ | H | 110° |
| 4 | $CH_3$ | $CH_3$ | $CH_3$ | H | $NO_2$ | 4-Br | H | Foam |
| 5 | $CH_3$ | $CH_3$ | $CH_3$ | H | $NO_2$ | 4-$OSO_2CH_3$ | H | 128° |
| 6 | $CH_3$ | $CH_3$ | $CH_3$ | H | $NO_2$ | 4-$SCH_3$ | H | 104–6° |
| 7 | $CH_3$ | $CH_3$ | $CH_3$ | H | $NO_2$ | 4-F | H | 137° |
| 8 | $CH_3$ | $CH_3$ | $CH_3$ | H | $NO_2$ | 4-$SO_2CH_3$ | H | 124° |
| 9 | $CH_3$ | $CH_3$ | $C_2H_5$ | H | $NO_2$ | 4-Cl | H | Foam |
| 10 | $CH_3$ | $CH_3$ | $C_2H_5$ | H | $NO_2$ | 4-$OSO_2CH_3$ | H | 115° |
| 11 | $CH_3$ | $CH_3$ | $CH_3$ | H | $CF_3$ | 4-F | H | 86° |
| 12 | $CH_3$ | $CH_3$ | $CH_3$ | H | $NO_2$ | 4-$CF_3$ | H | 102–103.5° |
| 13 | $CH_3$ | $CH_3$ | $CH_3$ | H | $NO_2$ | 4-$SO_2CH_2Cl$ | H | |
| 14 | $CH_3$ | $CH_3$ | $CH_3$ | H | $NO_2$ | 4-$SO_2C_2H_5$ | H | |
| 15 | H | H | $C_2H_5$ | E | $NO_2$ | 4-Cl | H | |
| 16 | H | H | n-$C_3H_7$ | H | $NO_2$ | 4-Cl | H | |
| 17 | H | H | n-$C_4H_9$ | H | $NO_2$ | 4-Cl | H | |
| 18 | H | H | n-$C_4H_9$ | H | $NO_2$ | 4-$CF_3$ | H | |
| 19 | $CH_3$ | H | n-$C_3H_7$ | H | $NO_2$ | 4-Cl | H | |
| 20 | $CH_3$ | H | n-$C_3H_7$ | H | $NO_2$ | 4-$CF_3$ | H | |
| 21 | $CH_3$ | $CH_3$ | $CH_3$ | H | $NO_2$ | H | H | 87.5° |
| 22 | $CH_3$ | $CH_3$ | $CH_3$ | H | $NO_2$ | $OCHF_2$ | H | 95–99° |
| 23 | $CH_3$ | $CH_3$ | $CH_3$ |  | $NO_2$ | Cl | H | 115°* |
| 24 | $CH_3$ | $CH_3$ | $CH_3$ | H | $NO_2$ | Cl | 3-$OC_2H_5$ | 83.5° |
| 25 | $C_2H_5$ | $CH_3$ | $CH_3$ | H | $NO_2$ | Cl | H | oil |
| 26 | $CH_3$ | $CH_3$ | n-$C_3H_7$ | H | $NO_2$ | Cl | H | foam |
| 27 | $CH_3$ | $CH_3$ | $CH_3$ | H | Cl | Cl | H | 75° |
| 28 | $CH_3$ | $CH_3$ | i-$C_3H_7$ | H | $NO_2$ | Cl | H | foam |
| 29 | $CH_3$ | $CH_3$ | $CH_3$ | H | $NO_2$ | $OCF_3$ | H | 73–75.5° |

*as mixture of Ib and Id forms
NMR Spectra
Compound 4
$^1$H nmr (CDCL$_3$): δ 1.30, 1.53(s, s, 6H, C(CH$_3$)$_2$), 3.08, 3.38(s, s, 3H, NCH$_3$) 7.21(d, 1H, 8Hz), 7.83(dd, 1H, 8Hz), 8.33(d, 1H, 2Hz-phenyl H)
Compound 9
$^1$H nmr (CDCL$_3$): δ 1.33, 1.53(s, s, 6H, C(CH$_3$)$_2$), 1.20(m, 3H,NCH$_2$CH$_3$), 3.66(m, 2H, NCH$_2$CH$_3$), 7.28(d, 1H, 8Hz), 7.66(dd, 1H, 8Hz), 8.18(d, 1H, 2Hz-phenyl H).

EXAMPLE 2

Preparation of 2,6-dimethyl-5-(4-chloro-2-nitrobenzoyloxy)-6H-1,2-oxazine- 3-one (formula IIa, $R_1$=$R_3$=$CH_3$, $R_2$=$R_6$=H, R=$NO_2$, $R_5$=Cl)

To a solution of 1.77 g of 2,6-dimethyl-2H-1,2-oxazine-3,4(4H,6H)-dione in 15 ml of dichloromethane containing 2.4 ml of triethylamine is added dropwise at 0° C. a solution of 2.72 g of 4-chloro-2-nitrobenzoyl chloride in 10 ml of dichloromethane. After the addition is complete, the reaction mixture is stirred at r.t. for one hour, then diluted with dichloromethane, washed, dried and evaporated to dryness to give the title compound.

EXAMPLE 3

Preparation of 2,6-dimethyl-2H-1,2-oxazine-3,5(4Y,6H)-dione (Formula III $R_1$=$R_3$=$CH_3$, $R_2$=H)

4.9 g of an oily mixture of 2,6-dimethyl-4-carbomethoxy-2H-1,2-oxazine- 3,5(4H,6H)-dione and 2,6-dimethyl-4-carboethoxy-2H-1,2-oxazine- 3,5(4H,6H)-dione is obtained e.g. as illustrated below is heated at 79° C. in 25 ml of DMSO and 0.9 ml of water for 3 hours. The reaction mixture is taken up in ether, poured into water and extracted thoroughly with ether. The combined extracts are dried and evaporated to give 2,6-dimethyl-2H-1,2-oxazine- 3,5(4H, 6H)-dione.

The following tow diones may be prepared analogously.
2,6,6-trimethyl-2H-1,2-oxazine-3,5(4H,6H)-dione (Formula III $R_1$=$R_2$=$R_3$=$CH_3$)
2-ethyl-6,6-dimethyl-2H-1,2-oxazine-3,5-(4H,6H)-dione (Formula III $R_1$=$R_2$=$CH_3$, $R_3$=$C_2H_5$).

EXAMPLE 4

Preparation of 2,6-dimethyl-4-carbomethoxy-2H-1,2-oxazine-3,5(4H,6H)-dione and 2,6-dimethyl-4-carboethoxy-2H-1,2-oxazine-3,5(4H,6H)-dione as a mixture.

To a suspended solution of sodium methoxide, freshly prepared from 694 mg of sodium metal and methanol, in 45 ml of toluene is added dropwise at r.t. a solution of 7.1 g of methyl N-ethoxycarbonylacetyl-2-methylaminooxypropionate, in 10 ml of toluene. After completing the addition, the resulting mixture is stirred at r.t. for 24 hours. The reaction mixture is poured into ice-water and extracted with ether (discarded). The aqueous solution is then acidified with 10% aqueous HCL and extracted with dichloromethane. The combined extracts were dried and evaporated to dryness to yield an oily mixture of the title compounds.

EXAMPLE 5

Preparation of methyl N-ethoxycarbonylacetyl-2-methylaminooxypropionate

To a solution of 5.32 g of methyl 2-methylaminooxypropionate in 50 ml of dichloromethane is added dropwise at 0° C. a solution of 6.62 g of ethylmalonyl chloride in 15 ml of dichloromethane. After the addition is complete, the resulting solution is stirred at 0° C. for additional one hour. The reaction mixture is poured into water, and extracted with ether. The combined extracts are washed with dilute HCL, brine, dried and evaporated to give an oily residue which is chromatographed on silica gel to yield oil methyl N-ethoxycarbonylacetyl-2-methylaminooxypropionate.

NMR spectra for the compounds of examples 2 to 5.

Example 2

$^1$H nmr (CDCL$_3$): δ 1.47 (d,3H,OCH(CH$_3$)), 3.20 (s,3H, NCH$_3$), 4.81 (q,1H,OCH(CH$_3$)), 6.15 (s,1H,=CHCO) and 7.77, 7.97 (s,dd,3H,phenyl H).

Example 3

$^1$H nmr (CDCL$_3$): δ 1.43 (d,3H,OCH(CH$_3$)), 3.30 (S,1H, NCH$_3$), 3.53 (q,2H,OCCH$_2$CO) and 4.40 (q,1H,OCH$_3$)).

Example 4

2,6-dimethyl-4-carbomethoxy-2H-1,2-oxazine-3,5(4H, 6H)-dione $^1$H nmr (CDCL$_3$): δ 1.50 (d,3H,OCH(CH$_3$)), 3.21 (s,3H, NCH$_3$), 3.93 (2,3H,OCH$_3$), and 4.73 (q,1H,OCH(CH$_3$)).

2,6-dimethyl-4-carboethoxy-2H-1,2-oxazine-3,5(4H, 6H)-dione $^1$H nmr (CDCL$_3$): δ 1.40 (t,3H,OCH$_2$CH$_3$), 1.48 (d,3H, OCH(CH$_3$)), 3.21 (s,3H,NCH$_3$), 4.41 (q,2H,OCH$_3$CH$_3$) and 4.73 (q,1H,OCH(CH$_3$)).

Example 5

Methyl N-ethoxycarbonylacetyl-2-methylaminooxypropionate $^1$H nmr (CDCL$_3$): δ 1.28 (t,3H,OCH$_2$CH$_3$), 3.23 (s,3H, NCH$_3$), 3.70 (q,2H,OCCH$_2$CO), 3.77 (s,3H,OCH$_3$), 4.21 (q,2H,OCH$_2$CH$_3$) and 4.57 (q,1H,OCH(CH$_3$).

I claim:

1. A pesticidal composition comprising a compound having the formula Ia

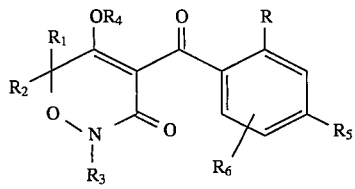

wherein each of $R_1$, $R_2$ and $R_3$ is independently hydrogen, $C_{1-8}$alkyl, carboxyl, $C_{1-8}$alkoxycarbonyl, phenyl or phenyl substituted by one to three groups as $R_5$, or $R_1$ and $R_2$ together form a $C_{3-6}$alkylene bridge;

$R_4$ is hydrogen, $C_{1-8}$alkyl, $C_{1-8}$aklylcarbonyl, $C_{1-8}$alkoxycarbonyl, —C(O)NR$_7$R$_8$, $C_{1-8}$-alkylsulphonyl, P(O)—(OR$_9$)$_2$, R$_7$P(O)—OR$_9$, benzoyl or a cation;

R is $C_{1-8}$alkyl optionally substituted by 1 to 6 halogen atoms, $C_{1-8}$alkoxy optionally substituted by 1 to 6 halogen atoms, $C_{1-8}$alkylcarbonyl, $C_{1-8}$alkoxycarbonyl, NR$_7$R$_8$, O$_n$S(O)$_n$R$_{10}$, NR$_7$SO$_2$R$_8$, halogen, cyano or nitro;

each of $R_5$ and $R_6$ is independently hydrogen or selected from the meanings given for R; or $R_5$ and $R_6$ together form the group —Y—W—Z—;

each $R_7$ and $R_8$ is independently hydrogen or $C_{1-8}$alkyl;

$R_9$ is $C_{1-8}$alkyl;

$R_{10}$ is $C_{1-8}$alkyl optionally substituted by 1 to 6 halogen atoms;

W is —(CR$_{11}$R$_{12}$)$_{t}$-(CR$_{13}$R$_{14}$)$_{t'}$ or sulphonyl;

each of Y and Z is independently oxygen, sulphur, sulphonyl, carbonyl or CR$_7$R$_8$ with the proviso that Y and Z are attached to adjacent carbon atoms;

each of $R_{11}$ and $R_{12}$ is independently hydrogen, halogen or $C_{1-8}$alkyl optionally substituted by 1 to 6 halogen atoms or together form an oxo group;

each of $R_{13}$ and $R_{14}$ is independently hydrogen, halogen or $C_{1-8}$alkyl optionally substituted by 1 to 6 halogen atoms;

n is 0 or 1;

n' is 0, 1 or 2;

t is 1 or 2;

t' is 0 or 1, in association with an agriculturally acceptable diluent or carrier.

2. A composition according to claim 1 wherein in formula Ia, the meanings of each of R, $R_1$, $R_2$, $R_3$, $R_4$, $R_5$ and $R_6$ are selected from one or more of the following for $R_1$, $R_2$, $R_3$ a) hydrogen or $C_{1-4}$alkyl;

b) hydrogen or $C_{1-4}$alkyl;

for R, a) $C_{1-4}$alkyl optionally substituted with chloro, bromo, or fluoro, —(O)$_n$—S(O)$_n$—C$_{1-4}$alkyl, halogen or nitro;

b) CH$_3$, CF$_3$, C$_{1-3}$alkylsulphonyl, C$_{1-3}$alkylsulphonyloxy, chloro, bromo or nitro;

for $R_5$, a) bromo, chloro, fluoro, haloalkyl, haloalkoxy, SC$_{1-4}$alkyl, OSO$_2$C$_{1-4}$-alkyl, SO$_2$C$_{1-4}$-alkyl, OSO$_2$—, C$_{1-4}$haloalkyl, NR$_7$SO$_2$C$_{1-4}$alkyl, or, together with R$_6$ the group —Y—W—Z—;

b) bromo, chloro, fluoro, trifluoromethyl, SC$_{1-4}$alkyl, OSO$_2$C$_{1-4}$alkyl, SO$_2$C$_{1-4}$alkyl, OSO$_2$C$_{1-4}$haloalkyl, NR$_7$SO$_2$C$_{1-4}$alkyl, or, together with R$_6$ the group —Y—W—Z—;

c) chloro, $C_{1-3}$alkylsulphonyl, $C_{1-3}$alkylsulphonyloxy or, together with R$_6$, —O—CH$_2$—O—;

d) chloro, fluoroalkyl, fluoroalkoxy, $C_{1-3}$alkylsulphonyl, $C_{1-3}$alkylsulphonoxy or together with R$_6$ —O—CH$_2$—O—;

for $R_6$, a) hydrogen, $C_{1-4}$alkyl, $C_{1-4}$alkoxy, bromo, chloro or, together with R$_5$ the group —Y—W—Z—;

b) hydrogen, methoxy, chloro or, together with R$_5$, —O—CH$_2$—O—;

for $R_4$, a) H, $C_{1-4}$alkyl, $C_{4-8}$alkylcarbonyl, benzoyl, $C_{1-4}$alkylsulphonyl or a cation;

b) hydrogen or Na$^+$, K$^+$, Li$^+$ or an ammonium cation;

c) CH$_3$, C$_2$H$_5$, t-butylcarbonyl, isobutylcarbonyl, benzoyl or methylsulphonyl.

3. A composition according to claim 1 wherein in formula Ia the meanings of each of R, $R_1$, $R_2$ $R_3$, $R_4$, $R_5$, $R_6$ and $R_{10}$ are selected from one or more of the following for $R_1$ and $R_2$ a) H, $C_{1-4}$alkyl, phenyl or phenyl substituted by one to three groups as $R_5$;

b) H, $C_{1-4}$alkyl, phenyl or phenyl substituted by one to three groups as R;

c) H, $C_{1-3}$alkyl;

d) H, CH$_3$;

e) $C_{1-3}$alkyl;

for $R_3$
   a) $C_{1-8}$alkyl;
   b) $C_{1-4}$alkyl;
   c) $CH_3$, $C_2H_5$;
for $R_4$ H;
for R,
   a) $NO_2$, Cl, $CF_3$;
   b) $NO_2$, Cl;
   c) $NO_2$
for $R_5$,
   a) Cl, Br, F, $CF_3$, $SO_2R_{10}$, $SR_{10}$, $OSO_2R_{10}$;
   b) Cl, Br, F, $CF_3$, $OCF_3$, $OCF_3H$, $SO_2R_{10}$, $SR_{10}$, $OSO_2R_{10}$;
   c) Cl, $CF_3$, $OSO_2R_{10}$, $SO_2R_{10}$;
   d) Cl, $CF_3$, $OCF_3$, $OCF_2H$, $OSO_2R_{10}$, $SO_2R_{10}$;
   e) Cl, $OSO_2R_{10}$;
   f) Cl, $SR_{10}$, $OCF_3$, $OCF_2H$;
for $R_6$, H;
for $R_{10}$,
   a) $C_{1-5}$alkyl optionally halogen substituted;
   b) $C_{1-3}$alkyl optionally halogen substituted;
   c) $C_{1-3}$alkyl.

4. A composition according to claim 3 wherein in formula Ia $R_1$, $R_2$ and $R_3$ are each methyl, $R_4$ and $R_6$ are each hydrogen, R is nitro and $R_5$ is chloro, $SCH_3$, $OSO_2CH_3$ or $SO_2CH_3$.

5. A composition according to claim 3 wherein in formula Ia $R_1$, $R_2$ and $R_3$ are each methyl, $R_4$ and $R_6$ are each hydrogen, R is nitro and $R_5$ is chloro, $SCH_3$, $OCF_3$ or $OCF_2H$.

6. A composition according to claim 1 wherein in formula Ia $R_1$, $R_2$ and $R_3$ are each methyl, $R_4$ and $R_6$ are hydrogen, R is nitro and $R_5$ is chloro.

7. A composition according to claim 1 wherein in formula Ia $R_1$, $R_2$ and $R_3$ are each methyl, $R_4$ and $R_6$ are hydrogen, R is nitro and $R_5$ is trifluoromethoxy.

8. A composition according to claim 1 wherein in formula Ia $R_1$, $R_2$ and $R_3$ are each methyl, $R_4$ and $R_6$ are each hydrogen, R is nitro and $R_5$ is selected from hydrogen, fluoro, chloro, bromo, methylthio, methylsulfonyl, ethylsulfonyl, methylsulfonyloxy, chloromethylsulfonyl, trifluoromethyl, difluoromethoxy or trifluoromethoxy.

9. A composition according to claim 8 wherein in formula Ia $R_5$ is selected from hydrogen, fluoro, chloro, bromo, methylthio, methylsulfonyl, methylsulfonyloxy, trifluoromethyl, difluoromethoxy or trifluoromethyoxy.

10. A composition according to claim 1 wherein in formula Ia R is nitro, $R_4$ and $R_6$ are each hydrogen, $R_5$ is chloro and $R_1$ is selected from hydrogen, methyl or ethyl, $R_2$ is selected from hydrogen or methyl and $R_3$ is selected from methyl, ethyl, propyl or butyl whereby all of $R_1$, $R_2$ and $R_3$ are not simultaneously methyl.

11. A composition according to claim 10 wherein in formula Ia $R_1$ is selected from methyl or ethyl, $R_2$ is selected from hydrogen or methyl and $R_3$ is selected from methyl, ethyl or propyl whereby all of $R_1$, $R_2$ and $R_3$ are not simultaneously methyl.

12. A composition according to claim 1 wherein in formula Ia $R_4$ and $R_6$ are each hydrogen and $R_1$ and $R_2$ are selected from hydrogen or methyl, $R_3$ is selected from methyl, ethyl, propyl or butyl, R is selected from nitro, chloro or trifluoromethyl and $R_5$ is selected from fluoro, chloro, trifluoromethyl, methylsulfonyl or methylsulfonyloxy whereby when R is nitro, $R_5$ is other than chloro.

13. A composition according to claim 12 wherein n formula Ia $R_1$ and $R_2$ are methyl, $R_3$ is selected from methyl or ethyl, R is selected from nitro, chloro or trifluoromethyl and $R_5$ is selected from fluoro, chloro, methylsulfonyl or methylsulfonyloxy whereby when R is nitro, $R_5$ is other than chloro.

14. A composition according to claim 1 wherein $R_1$, $R_2$ and $R_3$ are each methyl, R s nitro, $R_5$ is chloro and
   a) $R_4$ is hydrogen and $R_6$ is 3-ethoxy; or
   b) $R_4$ is benzoyl and $R_6$ is hydrogen.

15. A method of controlling weeds comprising applying to the weeds or their locus a herbicidally effective amount of a composition according to claim 1.

* * * * *